United States Patent

Althainz et al.

[11] Patent Number: 5,783,154
[45] Date of Patent: Jul. 21, 1998

[54] SENSOR FOR REDUCING OR OXIDIZING GASES

[75] Inventors: Peter Althainz, Kalrsruhe; Joachim Goschnick, Mühlacker, both of Germany

[73] Assignee: Forschungszentrum Karlsruhe GmbH, Karlsruhe, Germany

[21] Appl. No.: 747,252

[22] Filed: Nov. 18, 1996

Related U.S. Application Data

[63] Continuation-in-part of PCT/EP95/01799, May 12, 1995.

[30] Foreign Application Priority Data

Jul. 2, 1994 [DE] Germany .................. 44 23 289.6

[51] Int. Cl.[6] .................................................. G01N 25/16
[52] U.S. Cl. .................. 422/98; 422/90; 422/94; 422/95; 422/97; 73/23.2; 73/23.31; 73/23.32; 73/23.34; 73/31.03; 73/31.05; 73/31.06; 338/24
[58] Field of Search .................... 422/90, 94–95, 422/97, 98; 73/23.2, 23.31, 23.32, 23.34, 31.03, 31.05, 31.06; 338/24

[56] References Cited

U.S. PATENT DOCUMENTS

| 4,007,435 | 2/1977 | Tien | 338/34 |
|---|---|---|---|
| 4,377,944 | 3/1983 | Hishii et al. | 73/31.06 |
| 4,457,161 | 7/1984 | Iwanaga et al. | 73/23 |
| 4,654,624 | 3/1987 | Hagan et al. | 338/34 |
| 4,697,165 | 9/1987 | Ishiguro et al. | 338/34 |
| 4,928,513 | 5/1990 | Sugihara et al. | 73/16 |
| 5,045,285 | 9/1991 | Kolesar, Jr. | 422/98 |
| 5,367,283 | 11/1994 | Lauf et al. | 422/90 |
| 5,451,371 | 9/1995 | Zanini-Fisher et al. | 422/51 |

FOREIGN PATENT DOCUMENTS

| 0 364 315 | 4/1990 | European Pat. Off. . |
| 2 170 913 | 8/1986 | United Kingdom . |

OTHER PUBLICATIONS

Althainz, et al., Gas sensor micro system for simultaneous defection of gases in the atmosphere. KFK-Nachr. (1994), 26(1) 42–51.

M.S. Nayak, et al., "Transformed Cluster Analysis: An Approach to the Identification of Gases–Odor Using an Integrated Gas–Sensor Array", Sensors and Actuators, 1993, Bd. 12, pp. 103–110.

Primary Examiner—Jill Warden
Assistant Examiner—Sharidan Carrillo
Attorney, Agent, or Firm—Klaus J. Bach

[57] ABSTRACT

In a gas sensor for sensing reducing or oxidizing gases which comprises a semiconductive metal oxide film, there are provided stripe-like outer electrodes which define therebetween a continuous surface area and stripe-like inner electrodes which extend between, and parallel to, the outer electrodes so as to divide the continuous surface area into longitudinal segments which have different properties with respect to reducing or oxidizing gases such that different conductivity changes are generated for the different segments upon exposure to oxidizing or reducing gases.

6 Claims, 4 Drawing Sheets

SENSOR FOR REDUCING OR OXIDIZING GASES

This is a Continuation-in-Part application of International application PCT/EP95/01799 filed May 12, 1995 and claiming the priority of German application P 44 23 289.6 filed Jul. 2, 1994.

BACKGROUND OF THE INVENTION

The invention relates to a gas sensor for reducing or oxidizing gases which comprises a substrate with several thin gas sensitive areas consisting of a semi-conductive metal oxide film.

Such a gas sensor is known from the publication by X. Wang, S. Yee and P. Carey, "Sensors and Actuators", B, 13–14 (1993), p. 458–461. The gas sensor described therein comprises eight sensor elements which are arranged in pairs on a silicon chip. Each of the sensor elements includes one or more of the semiconductive oxides $SnO_2$, $ZnO$, $TiO_2$, and $WO_3$, which are deposited as thin films on the chip. Some of the sensor elements are covered with palladium serving as a catalyst. All sensor elements differ in their composition or in their structural organization. When they are in contact with the gases to be measured the conductivity of the semiconductive oxides changes dependent on their compositon and, if applicable, on the catalyst disposed thereon. As a result each sensor element in contact with the gas to be measured provides a different signal proportional to the change of conductivity thereof. The conductivity changes of all the sensor elements are measured and, after calibration of the gas sensor by mathematical methods, are assigned to the concentration of one or several components of the gas to be measured. The measuring temperature is 200° C. It is indicated that the vapor or gaslike components methanol, acetone, benzene, toluene, TCE and CO in the gas can be analytically measured.

The manufacture of such a gas sensor appears to be difficult however, since all the sensor elements must be separately manufactured and each must be provided with two electrodes.

A similar gas sensor is known from the publication of M. S. Nayak, R. Dwivedi and S. K. Srivastava in "Sensors and Actuators", B, 12 (1993), pages 103–110. This publication provides the theoretical basis for the evaluation of a gas sensor which comprises a number of sensor elements.

In a publication by H. V. Shermer, J. W. Gardner and P. Corcoran in "Sensors and Actuators" B1, (1990), pages 256–260, a gas sensor with twelve tin oxide sensor elements is described. The sensor elements have all different characteristics. The publication discloses the electrical circuitry for the sensor elements whereby a gas mixture can be analytically determined.

From the publication by P. Althainz, A. Dahlke, M. Frietsch-Klarkopf, J. Goschink and H. J. Ache, "Physics Status Solids" (a) 145, 6111 (1994), a gas sensor for organic gases is known which includes a silicon dioxide substrate provided with a gas sensitive layer of tin oxide. On the gas sensitive layer, gold electrodes are disposed by means of which the conductivity changes of the gas sensitve layer which is in contact with a gas to be measured can be determined. The manufacture of the sensor by thin-film techniques is described in detail.

DE 36 10 363 A1 discloses a method for the continuous measuring of concentrations of gaseous components in gas mixtures with the exception of oxygen. This method utilizes electrochemical cells whose electrodes consist of metal oxides. The electrodes may be covered in part by a catalyst layer or they may be of different compositions. In this case however, the electrodes must be separated from one another by an inert material.

It is the object of the present invention to provide a gas sensor of the type referred to above which however is easy to manufacture. With such a sensor reducing gases such as hydrogen, methane, carbon dioxide, ethanol in its vapor phase etc., and oxidizing gases such as nitrogen dioxide should be determinable analytically that is it should be possible to identify the different components in a mixture of several components and quantitatively determine them.

SUMMARY OF THE INVENTION

In a gas sensor for sensing reducing or oxidizing gases which comprises a semiconductive metal oxide film, there are provided stripe-like outer electrodes which define therebetween a continuous surface area and stripe-like inner electrodes which extend between, and parallel to the outer electrodes so as to divide the continuous surface area into longitudinal segments which have different properties with respect to reducing or oxidizing gases such that different conductivity changes are generated for the different segments upon exposure to oxidizing or reducing gases.

With the designation of the gases as reducing or oxidizing gases, it is to be made clear that, in principle, all gases can be analytically determined with the sensor according to the invention with the exception of inert gases such as nitrogen, carbon dioxide or noble gases. In contrast to the gas sensors described above, the layer of the gas sensor according to the invention, which is sensitive to the gas to be measured or rather its components, is a single contiguous layer comprising one or several semiconductive oxides such as tin oxide. The contiguous layer is divided into separate segments by stripe-like electrodes. The outer electrodes define the total surface area of the contiguous layer whereas the inner electrodes divide the contiguous layer into different segments.

In contrast to the prior art sensor described earlier which needs 2n (n is the number of segments) electrodes, the sensor according to the invention requires only (n+1) electrodes. The electrodes can be disposed directly on, or below, the surface of the contiguous layer. Preferably, the electrodes are stripe-like and extend parallel to one another and over the full width of the contiguous layer. The electrodes form a parallel pattern which separates the various segments. The changes of the electric conductivity which is influenced by the type and concentration of the gas being measured can be determined by measuring the conductivity of the segments which are enclosed by the respective electrodes. The arrangement according to the invention has therefore substantially greater circuit structure capabilities available for analysis purposes than the gas sensor structure described initially.

For example, resistance measurements can be performed between two adjacent electrodes or between four electrodes. Because of the large number of segments with only little differences between adjacent segments, there is a redundancy of data so that faulty segments can be recognized by much different behavior. Finally, it is possible to measure integrally over several or all the segments by utilizing only the respective outer electrodes. In this way, distinguishing properties cannot be determined, but the sensitivity is greatly improved.

With the arrangement according to the invention, it is further possible to heat the sensors as will be described further below. Of the many particular electrodes, several electrodes (in a particular example, the two outer ones) can be provided with contact surfaces to provide for electrical contacts at both ends of an electrode so that not only the resistance of the segment, but also the resistance of the platinum contact strip itself can be measured. This feature is used for accurate temperature determination and control (platinum resistance thermometer).

In order to be able to determine analytically several components of a gas to be measured the segments have to differ in their structural organization or in their composition so that for each segment a conductivity is obtained which is different from that of any other segment when the sensor is contacted by one particular gas. The different conductivity change can be obtained by different composition or different doping of the semiconductor metal oxide layer.

In this case, each particular segment may be homogeneous within but different from any other segment. Such an arrangement may be provided by doping the metal oxide film by vapor deposition of precious metals through a planar mask which is moved, during the vapor deposition, stepwise to the side across the segments so that each segment is subjected to vapor deposition for a different period. As a result, the doping concentration is different for each segment.

In an alternative arrangement, the composition of the surface changes continuously over the whole area. Such a surface can be made by gas phase deposition (Chemical Vapor Deposition CVD) if, for example, two sources are provided of which one is arranged over a first and the other is arranged over a second end of the area to form the continuous surface. The gas phase deposition procedure also permits to control the chemical composition in a molecule layered fashion. To the end, precursor substances are vaporized and are converted, on a substrate by thermal or another energy transfer procedure to form the desired compound. With this method, a composition of the thin film is obtained which continuously changes from the first end of the continuous surface to the second end wherein at the ends the composition at the ends corresponds to the vapor sources disposed above the respective ends.

The different conductivity changing capabilities may also be achieved by different coatings of the continuous layer while the continuous layer itself may have a uniform composition. As such coatings, for example, the oxides $Al_2O_3$ or $SiO_2$ are suitable. However the permeability of the components of a gas to be measured may be influenced by the coating so that the contact of the various gas components with the various elements of the semiconductive metal oxide film is impaired to different degrees depending on the molecule structure.

The composition or thickness of the coating between the outer electrodes may continuously change. The change of the composition can be achieved by the gas phase deposition procedure referred to above. In the most simple case, a coating is applied to the continuous layer with a homogeneous composition whose thickness increases continuously from the location of the first outer electrode to the location of the second outer electrode so that, in cross-section, the coating is slightly wedge-shaped.

The gas sensor must be operated at a temperature of several hundred °C., for example between 300° and 400° C. It preferably includes therefore an integral heater. If the continuous surface is formed on a plate-like substrate such as a silicon chip, the opposite free side of the substrate may be provided with a meander-like heater strip. The heater strip may be applied by sputtering a suitable metal such as platinum onto the chip.

Since the temperature of the continuous layer also has an influence on the conductivity, the temperature effect can be utilized to change the conductivity. Several different heater strips may be applied to the free substrate surface wherein the area of the strips corresponds to one or several segments and they are assigned to these segments. In this manner, particular segments or groups of segments can be maintained at a temperature different from that of adjacent segments.

Finally, a chemically active layer can be provided which chemically converts the gas to be measured so that not the gas as such but a reaction product thereof is analytically measured. The reaction product needs to be a reducing or oxidizing gas.

The invention is described below on the basis of the enclosed drawings.

DESCRIPTION OF PREFERRED EMBODIMENTS

Figure 1C:
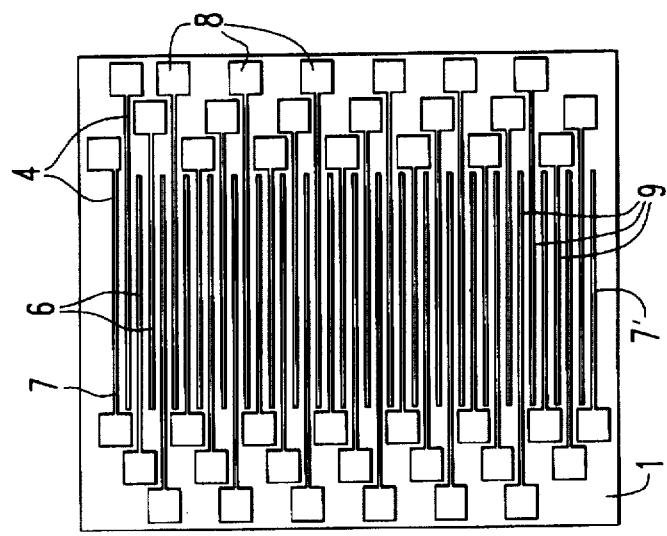
FIGS. 1a shows the bottom side and FIGS. 1b and 1c show top side arrangements of a substrate.
Figure 1B:
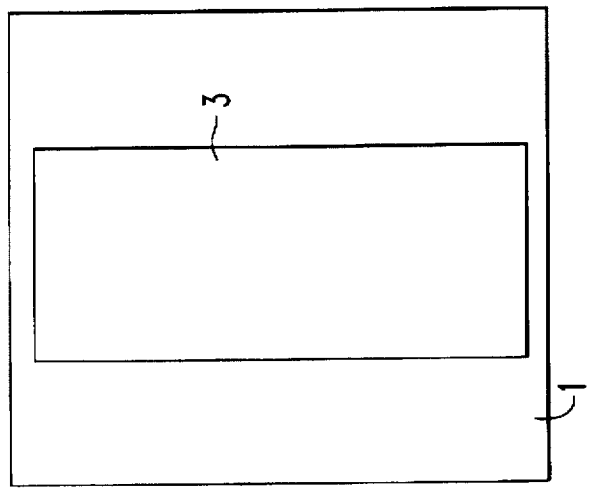
Figure 1A:
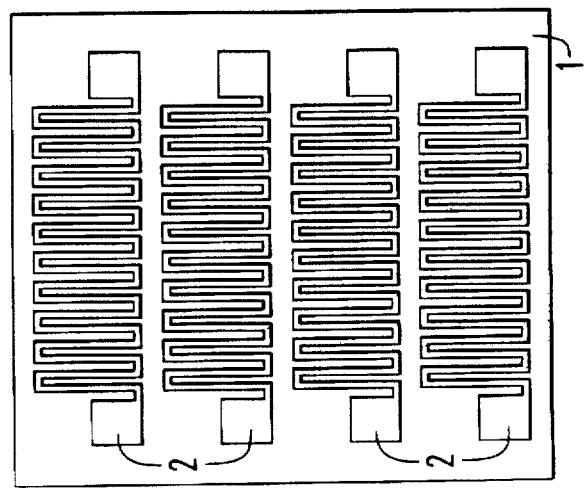

The sensor as shown in FIGS. 1a, 1b, and 1c is disposed on a plate-like substrate 1 which is a silicon wafer. FIG. 1a shows the underside of the substrate. On the underside, there are four heating elements 2 of platinum which have been deposited by sputtering. By means of the heating elements 2 segments of the substrate 1 can be maintained at different temperatures. FIGS. 1b and 1c show the top side of the substrate 1. FIG. 1b shows a continuous layer 3 of $SnO_2$. FIG. 1c shows an electrode strip structure 4 which extend over the full width of layer 3 and comprise outer electrodes 7, 7' and inner electrodes 9 which all have contact structures 8 at opposite ends. By means of the electrodes 4, the continuous layer 3 is divided into stripe-like, gas sensitive segments 6. The outer electrodes 7 and 7' extend adjacent opposite ends of the layer 3.

Figure 2:
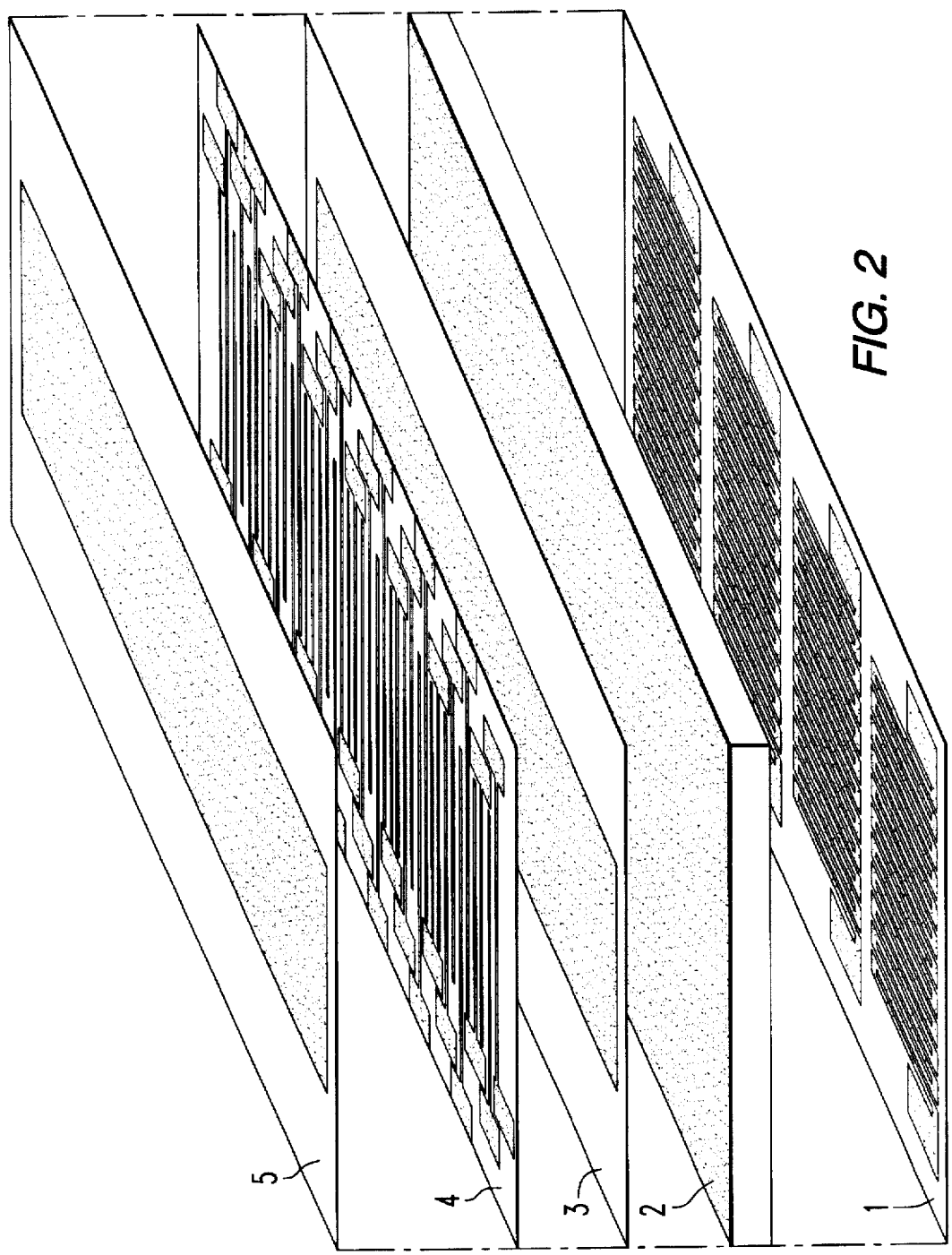
FIG. 2 shows a chip comprising various components in an exploded view.

The sensor as shown in the exploded view of FIG. 2 is provided with an additional layer 5. The thickness of the layer 5 changes uniformly between the two outer electrodes.

FIG. 3a–3d show various types of masks usable in the manufacture of the sensor shown in FIG. 2. All components of the sensor are made using the masks for covering parts of the surface of the wafer. The masks may consist for example of rectangular nickel sheets of 0.5 mm thickness. They may be made by microstructure techniques.

Figure 3A:
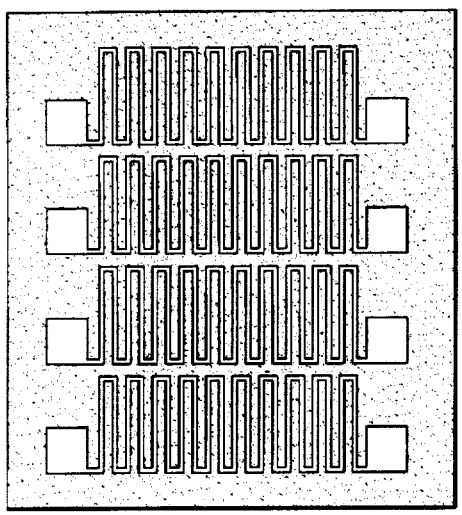
FIGS. 3a, 3b, 3c, and 3d show various masks for making the chip.
Figure 3B:
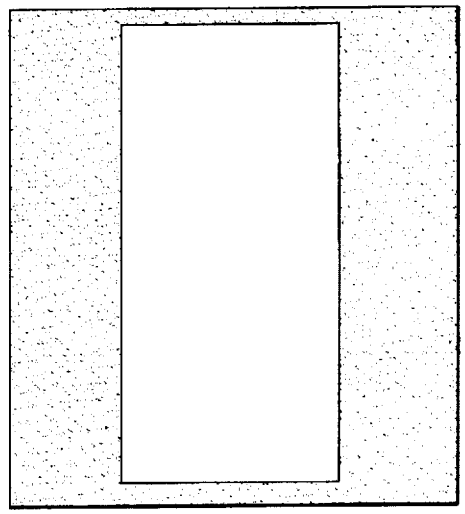
Figure 3C:
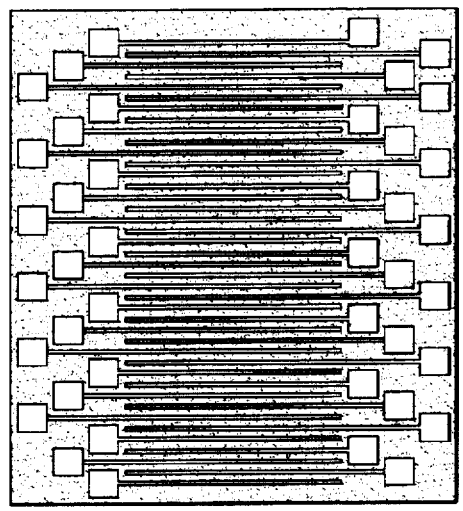
Figure 3D:
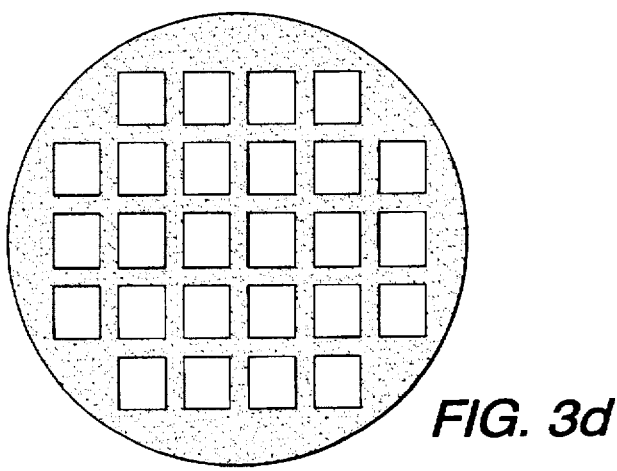
Figure 4C:
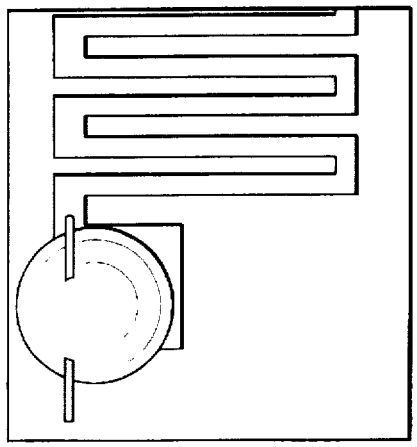
FIG. 4c shows the heater contact structure.
Figure 4F:
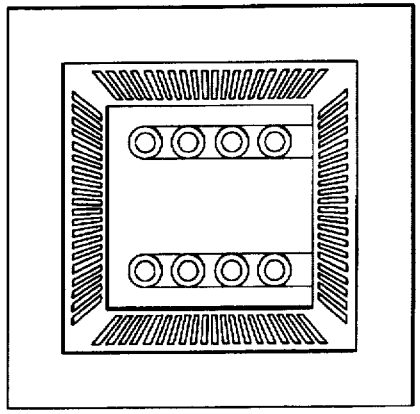
FIG. 4a shows an embodiment wherein a chip is disposed in a housing.
FIG. 4b is a partial view of a heater arrangement.
FIG. 4d shows the electrodes.
FIG. 4e shows the electrode contact areas and, FIG. 4f shows a housing with the chip disposed therein.
Figure 4B:
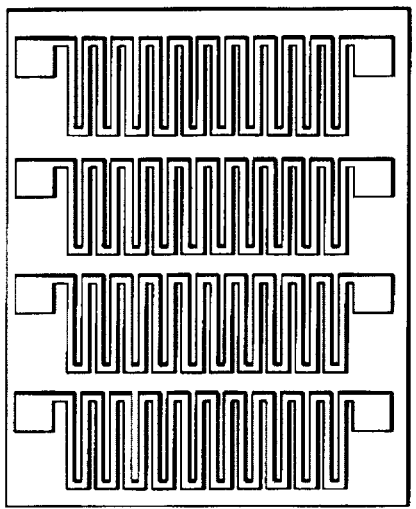
Figure 4E:
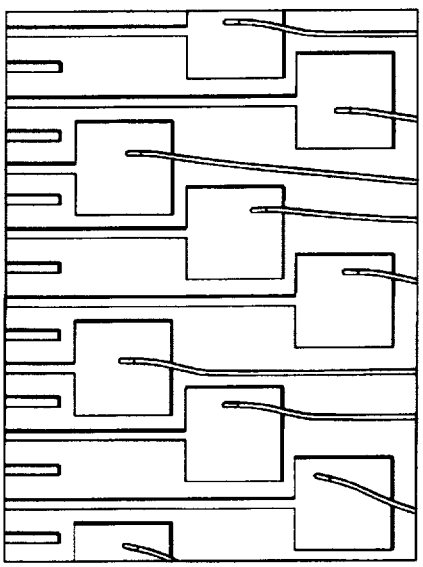
Figure 4A:
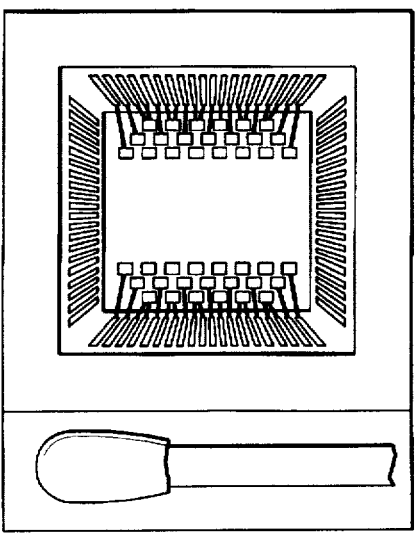
Figure 4D:
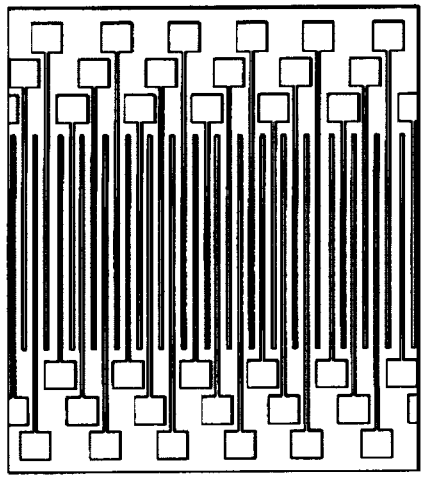

FIG. 3a, for example, shows a mask which is used for making a heating structure comprising four elements.

FIG. 4a to FIG. 4f are various views of a finished gas sensor.

Below, the invention will be described on the basis of some examples:

Example 1

Manufacture of the metal oxide layer, the electrodes and the heating elements of a gas sensor:

As starting material, a silicon wafer of 3 inch diameter and a thickness of 0.5 mm was used. On both sides of the wafer, there is a 500 nm $SiO_2$ layer to provide for electrical insulation. All layers with the exception of the lateral continuously changing coating on the segments were applied by a high frequency sputtering technique (magnetism sputtering). The surfaces were microstructured by metallic shading masks which have have a thickness of 0.05 mm and which have cutouts in those areas where material is to be deposited. The masks are fixed on the substrate wafer and both together are placed into a magnetron. On each disc, there is room for 26 separate sensors (FIG. 3d) of 8×9 mm each. Each of these sensors includes more than 40 stripe-like electrodes thereby providing for 39 segments. Each electrode has a width of 50 μm and the distance between adjacent electrodes is 150 μm.

First, meander-shaped heating elements of platinum with a thickness of 1000 nm are sputtered onto the back side of the wafer. To provide adherence, there is a 30 nm thick layer of titanium. Then, an Ag layer of several μm thickness is sputtered onto the bond surface.

After the heating elements are completed, the substrate is turned over and the mask for making the metal oxide film is mounted. An $SnO_2$ coating with a 150 nm thickness is provided by reactive magnetron sputtering with argon oxygen mixture of 80/20 with an energy input of 60 watts.

Then the mask for forming the electrode structure is mounted onto the wafer. First, the $SnO_2$ segments are covered up and a titanium bonding layer for the attachment of the bond surfaces is produced on the wafer. After removal of the cover, the actual platinum contact areas with a thickness of 1000 nm are sputtered onto the wafer. Finally, again a 1000 nm thick Ag layer is deposited on the bond surface areas to provide good contact areas for a conductor.

In the final step, the wafer is cut into the 26 chips. The so obtained sensor chips are installed in commercially available IC housings and the electrical connection to the chip are established by an ultrasound joining procedure with the aluminum wire (electrodes) and gold wires (heating elements).

Example 2

Manufacture of a gas sensor with, in a cross-section, wedge-shaped coating:

$SiO_2$ is manufactured by an ion beam-assisted gas phase deposition procedure (IBAD=ion beam assisted deposition). This method is described in a publication by P. Althainz, A. Dahlke, M. Frietsch-Klarhof, J. Goschnik and H. J. Ache, "Organically modified $SiO_2$ and $Al_2O_3$ films as selective components for gas sensors", Physica Status Solidi. In this method gaseous tetra-ethoxysilon (TEOS) is converted to $SiO_2$ by exposure to ion irradiation. The ion irradiation exposure can be limited, by a mask, to a small area so that $SiO_2$ is formed only in this small area. In this way, a layer with a thickness gradient was generated by using a 2 mm wide slot mask under which a substrate was continuously moved during the vapor deposition. The layer had lateral dimensions of 20×20 $mm^2$ and had at one end a thickness of 6 mm and at the other end a thickness of 8 mm.

Example 3

Manufacture of a sensor with continuously changing composition of the semiconductive metal oxide thin film:

It is possible to make a sensor with continuously changing composition of the semiconductive metal oxide thin film with an arrangement including two magnetron sputtering sources one of which generates $SnO_2$ and the other for example ZnO. A continuously changing composition can be obtained by arranging the two sputtering sources not parallel across the substrate surface but to the side thereof so that intentionally a non-homogeneous coating is provided by each of the sources wherein one source deposits more material in the area where the other deposits less and vice versa.

Example 4

Manufacture of a sensor with continuously changing composition of the coating covering the metal oxide thin film:

With ion beam based deposition also other oxide layers can be generated. In a publication by D. Leinen, A. Fernandez, J. P. Espinos, T. R. Belderrain and A. R. Gonzales-Elipe, "Ion Beam Induced Chemical Vapor Deposition for the Preparation of Thin Film Oxides", Thin Solid Films, 241 (1994) 198, the deposition for example of $TiO_2$ is described. A layer of varying composition covering the metal oxide film can be obtained by first admitting TEOS to the vacuum chamber and coating therewith, using an ion beam (argon 5 keV) and a slot mask starting at one end of the metal oxide film. While the slot mask is moved over the metal oxide film, the TEOS in the chamber is replaced, to an increasing degree, by titanium propylate [$Ti(CH_3CH_2O)_4$] which results in the formation of a mixed oxyd until, at the other end of the metal oxide film, the coating comprises pure $TiO_2$.

What is claimed is:

1. A gas sensor for reducing or oxidizing gases, comprising:
   a) a number of gas sensitive, longitudinal segments consisting of a semiconductive metal oxide film,
   b) each of said segments having two strip electrodes in contact therewith,
   c) said segments having different properties with respect to reducing or oxidizing gases such that different conductivity changes are generated from said segments upon exposure to oxidizing or reducing gases,
   d) said segments defining together a continuous surface area, and
   e) said strip electrodes including outer electrodes extending at opposite ends of said continuous surface area so as to limit said continuous surface area, and inner electrodes extending between, and parallel to, said outer electrodes so as to divide said continuous surface area into said longitudinal segments.

2. A gas sensor according to claim 1, wherein said metal oxide film is provided with a coating having a permeability for reducing or oxidizing gases which changes continuously between said outer electrodes.

3. A gas sensor according to claim 1, wherein said metal oxide thin film has a coating which reacts with the gas to be measured so as to convert said gas to a reducing or oxidizing gas.

4. A gas sensor according to claim 2, wherein said changing permeability for reducing and oxidizing gases is obtained by a continuously changing chemical composition of said coating.

5. A gas sensor according to claim 2, wherein said continuous surface area includes a metal oxide film which is doped in such a way that its composition changes continuously between said outer electrodes.

6. A gas sensor according to claim 1, wherein said continuous surface area is disposed on a first side of a substrate and meandering heating elements are disposed on a second side of said substrate, said heating elements being arranged opposite one or respective ones of said segments.

* * * * *